US006607778B2

(12) United States Patent
Mutka et al.

(10) Patent No.: US 6,607,778 B2
(45) Date of Patent: Aug. 19, 2003

(54) SOLID DELIVERY SYSTEMS FOR AROMA INGREDIENTS

(75) Inventors: Jerry Richard Mutka, Corona, CA (US); Robert Clark McIver, Tabernacle, NJ (US); Christine Ann Palmer, Whittier, CA (US); Daniel Benczedi, Geneva (CH); Pierre-Etienne Bouquerand, Pers-Jussy (FR); Antoine Firmenich, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/847,906

(22) Filed: May 3, 2001

(65) Prior Publication Data

US 2001/0038879 A1 Nov. 8, 2001

Related U.S. Application Data

(63) Continuation of application No. PCT/IB99/01777, filed on Nov. 3, 1999, which is a continuation-in-part of application No. 09/185,536, filed on Nov. 4, 1998, now abandoned.

(30) Foreign Application Priority Data

Nov. 9, 1998 (IN) ................................................ 3309/98

(51) Int. Cl.$^7$ ............................................. A23L 1/221
(52) U.S. Cl. ...................... 426/650; 426/103; 426/534; 426/651
(58) Field of Search ............................ 426/3, 650, 651, 426/89, 96, 103, 534

(56) References Cited

U.S. PATENT DOCUMENTS

| 3,704,137 | A | | 11/1972 | Beck ........................... 99/140 |
| 4,060,645 | A | | 11/1977 | Risler et al. ................. 426/302 |
| 4,070,381 | A | | 1/1978 | van den Ouweland ... 260/347.8 |
| 4,277,511 | A | * | 7/1981 | Bliznak et al. ............. 426/548 |
| 4,610,890 | A | | 9/1986 | Miller et al. ................. 426/651 |
| 4,707,367 | A | | 11/1987 | Miller et al. .................. 426/96 |
| 4,889,735 | A | | 12/1989 | Pickenhagen et al. ...... 426/536 |
| 5,009,900 | A | | 4/1991 | Levine et al. ................. 426/96 |
| 5,897,897 | A | * | 4/1999 | Porzio et al. ................. 426/96 |
| 5,972,395 | A | | 10/1999 | Saleeb et al. ................. 426/96 |

FOREIGN PATENT DOCUMENTS

| EP | 0 284 747 | 10/1988 |
| GB | 2 290 693 | 1/1996 |
| WO | 94/06308 | 3/1994 |
| WO | 98/03188 | 1/1998 |
| WO | 98/34495 | 8/1998 |

* cited by examiner

*Primary Examiner*—Leslie Wong
(74) *Attorney, Agent, or Firm*—Winston & Strawn

(57) ABSTRACT

The present invention relates to novel solid systems for the delivery of aroma chemicals and flavoring ingredients, including an extrusion formed matrix containing an effective amount of certain specific hydrophilic aroma materials. These systems are useful for flavoring consumer products. An extrusion of solid Furaneol® compound and derivatives that have a content of up to 40% by weight of Furaneol® compound are disclosed.

17 Claims, No Drawings

SOLID DELIVERY SYSTEMS FOR AROMA INGREDIENTS

This application is a continuation of the U.S. national phase designation of International Application No. PCT/IB99/01777 filed Nov. 3, 1999, the content of which is expressly incorporation herein by reference thereto, and the International application is a continuation-in-part of U.S. application Ser. No. 09/185,536 filed Nov. 4, 1998, now abandoned.

TECHNICAL FIELD AND PRIOR ART

The present invention relates to novel solid systems for the delivery of aroma chemicals and flavoring ingredients, which systems include a matrix formed by extrusion and containing an effective amount of a hydrophilic aroma ingredient, in particular of 3-hydroxy-4,5-dimethyl-2(5H)-furanone, 4-hydroxy-2,5-dimethyl-3(2H)-furanone, 4-hydroxy-5-methyl-3(2H)-furanone, 3-hydroxy-2-methyl-4(4H)-pyranone, 3-hydroxy-2-ethyl4(4H)-pyranone, 2-hydroxy-2-penten4-olide or a compound of formula

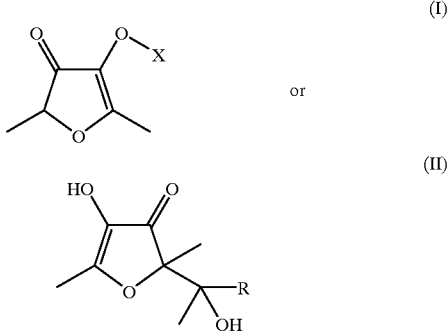

(I)

or (II)

wherein X designates a linear or branched, saturated or unsaturated $C_1$–$C_5$ hydrocarbon radical or a group of formula:

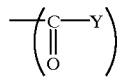

wherein Y designates a linear or branched, saturated or unsaturated $C_1$–$C_6$ hydrocarbon radical, and R represents a hydrogen atom, a methyl group, an acetyl group or an ethoxycarbonyl group.

It is well known in the food industry that the addition of flavoring ingredients contributes to a major extent to the palatability of consumable edible materials; consequently, it is paramount to ensure the production of food products which are of consistent flavor quality and are thus attractive to consumers. This can be achieved by ensuring proper flavor release. In effect, taste and aroma are greatly influenced by the volatile components present in such products. However, because of the volatility of these flavoring compounds, it is not easy to ensure that the predetermined critical amounts of each flavor component be present in the food and products as they reach the consumer. Losses of volatile components might occur during storage prior to incorporation into the food products, during mixing of the flavor component with the other food ingredients, during food processing, cooking, baking, during transportation and storage and finally during the preparation of the food product by the consumer himself.

These losses of volatile components from the food products may produce undesirable variations in the taste and aroma of the products as perceived by the consumer. On the other hand, losses of volatile components might occur through the conversion of certain flavor materials into unwanted, less desirable or tasteless chemicals by their interaction with reagents present in the environment. Oxygen is an example of this type of reagent, as it promotes the conversion of several labile flavor materials of current and critical utilization in the industry.

It is not surprising therefore to observe that, in order to reduce or eliminate the above-mentioned problems associated with volatile and labile flavor components, various attempts have been made to encapsulate such components in certain carbohydrate matrices so as to reduce the volatility or liability of the components. This results in the preparation of stable free flowing powders containing the flavor compositions for later flavor release when incorporated into the food products or when the food product is eventually consumed.

The prior art has therefore developed a number of techniques for producing solid essential oil compositions. Amongst these, extrusion methods typically rely on the use of carbohydrate matrix materials which are heated to a molten state and combined with the essential oils and flavor ingredients, before extruding and quenching the extruded mass to form a glass which protects the flavor.

One significant example of the prior art disclosure in this field is U.S. Pat. No. 3,704,137 which describes an essential oil composition formed by mixing oil with an antioxidant, separately mixing water, sucrose and hydrolyzed cereal solids with DE below 20, emulsifying the two mixtures together, extruding the resulting mixture in the form of rods into a solvent, removing the excess solvent and finally, adding an anti-caking agent.

Another, more pertinent example in the context of the invention is that of U.S. Pat. Nos. 4,610,890 and 4,707,367 which describe a process for preparing a solid essential oil composition having a high content of the essential oil, which composition is prepared by forming an aqueous solution containing a sugar, a starch hydrolysate and an emulsifier. The essential oil is blended with the aqueous solution in a closed vessel under controlled pressure to form a homogeneous melt, which is then extruded into a relatively cold solvent, dried and combined with an anti-caking agent.

The above-mentioned patents, and all the other prior art there-cited, are merely illustrative of the considerable volume of patent literature related to the fixation of flavor ingredients in various matrices and which, in essence, discloses the encapsulation of flavor materials in glass-like polymeric materials, in particular carbohydrate matrices.

Now, it is a typical and consistent feature of all the prior art in this field that the material encapsulated in the above-mentioned carbohydrate matrices consists of essential oils and/or oil-soluble flavor materials, such that the encapsulated composition is substantially hydrophobic, the methods and flavor delivery systems prior disclosed often resorting to the use of a suitable emulsifier to allow blending of the flavor oil with the aqueous matrix components cited above, so as to obtain an homogeneous melt which, upon cooling, forms the protecting glass.

To the best of our knowledge, there has never been any report in the prior art of the use of such matrices to encapsulate any significant amounts of hydrophilic flavor ingredients or flavor modifiers which are chemically reactive, i.e. which are sensitive to oxygen and moisture.

The prior known extruded solids are flavor delivery systems designed for the release of hydrophobic flavors and which are based on the knowledge that the long chains of carbohydrates, typically including maltodextrines, starches, hydrogenated starch hydrolysates, modified starches and/or gums, are plasticized with small molecular weight carbohydrates. The latter are typically disaccharides, sugar alcohols, polyols and similar substances. In addition, hydrophilic materials and solvents, namely water, also have the effect of plasticizing the matrix and lowering the glass transition temperature of the extruded solid. However, if the latter are present in quantities greater than a few percent, the matrix is destabilized and the protective effects of encapsulation are lost. As a result of this knowledge, hydrophilic flavor materials have never been encapsulated in carbohydrate matrices in any significant amount, and certainly never on their own, i.e. without being combined with, or diluted in, substantially hydrophobic flavor oils and compositions. It has in fact been a consistent assumption in the art that hydrophilic flavor materials used in significant amounts would plasticize the matrix to an unacceptable extent and destroy its capability of protecting the flavor material.

Yet, hydrophilic flavor materials which are labile flavor ingredients, easily decomposing and deteriorating in the presence of moisture, could ideally profit from the advantages of encapsulation in the above matrices and it goes without saying that any method which successfully provides for the stable encapsulation of such materials is of paramount importance for the flavor and food industries in particular, and can also be advantageous in perfumery

DESCRIPTION OF THE INVENTION

The present invention exactly provides a solution to this problem.

We have now discovered with surprise that, contrary to the common assumption in the art, it is possible to obtain extruded solids encapsulating chemically reactive hydrophilic aroma materials, on their own and in amounts which render such solids preferred and valuable flavors, capable of delivering effective amounts of hydrophilic flavor modifiers and ingredients.

One object of the present invention is therefore a solid delivery system for the release of aroma ingredients, comprising an extrusion formed matrix containing an effective amount of a substantially hydrophilic aroma material.

By an "effective amount of hydrophilic aroma material" it is understood here an amount of hydrophilic aroma material which is sufficient to confer, enhance, improve or modify the fragrance and/or the flavor of the consumer product into which the solid delivery system is incorporated.

The delivery systems of the invention provide uniform distribution of the hydrophilic flavor material in the matrix, thus stabilizing the latter during storage and use. The active aroma ingredient is in fact retained throughout the matrix in a homogeneous manner and thus becomes far more resistant to moisture degradation. Furthermore, as will become apparent from the description and examples hereafter, the handling of this aroma and its incorporation in compositions and consumer products is also greatly facilitated by its treatment according to the invention.

The matrix composition is based on the use of common polymeric saccharides, namely sugars and their derivatives.

The delivery systems of the invention do not require special equipment and can be prepared using any current single or twin-screw extruder typically used according to prior known "wet extrusion" or "dry blend" (also called "flash-flow") techniques, the latter requiring feeding of a melt of an originally mainly solid mass into the extruder, and the former the extrusion of a mainly fluid mass melt resulting from the prior solution of the matrix and the material to be encapsulated in a solvent, typically water.

The hydrophilic materials advantageously improved through production according to the invention can be selected amongst all the current flavor materials which are known to be hydrophilic. The examples given hereafter are meant to illustrate a variety of embodiments of the invention but are not to be interpreted as limiting the latter. These hydrophilic materials will be preferably used in the solid state, and this may require spray-drying of liquid or fluid aroma materials, or any other drying treatment, to render them solid prior to their admixture with the matrix and to the extrusion of the mixture.

More objects and aspects of the invention will become apparent from the detailed description hereafter.

According to a preferred embodiment of the above-cited delivery system of the invention, the latter consists essentially of the matrix and the hydrophilic aroma material. In other words, this preferred embodiment of the invention provides hydrophilic aroma materials, in solid form, obtained by extrusion methods. By extrusion methods we mean here methods according to which, typically, the matrix components, the hydrophilic aroma material and an emulsifier are heated, optionally in the presence of a plasticizer, to a temperature which allows the formation of an homogeneous melt, which is then quenched to form the solid product containing the hydrophilic aroma.

The aroma materials according to the invention will preferably be a hydrophilic flavor ingredient, or composition, of current use in the flavor industry. These are ingredients or compositions useful for imparting an odor and/or a flavor or taste to a consumer product traditionally flavored, or which are capable of modifying the odor and/or the taste of said consumer product. They will preferably be ingredients which are solid at room temperature. Nevertheless, hydrophilic materials which are liquid at room temperature can be solidified for example by spray-drying techniques, and then incorporated in the matrix.

In a preferred embodiment, such materials are selected from the group consisting of 3-hydroxy-4,5-dimethyl-2 (5H)-furanone, 4-hydroxy-2,5-dimethyl-3(2H)-furanone, 4-hydroxy-5-methyl-3(2H)-furanone, 3-hydroxy-2-methyl-4(4H)-pyranone, 3-hydroxy-2ethyl-4(4H)-pyranone, 2-hydroxy-2-penten-4-olide or a compound of formula:

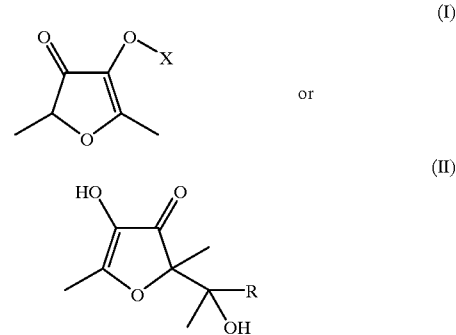

wherein X designates a linear or branched, saturated or unsaturated $C_1$–$C_5$ hydrocarbon radical or a group of formula:

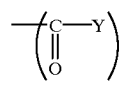

wherein Y designates a linear or branched, saturated or unsaturated $C_1$–$C_6$ hydrocarbon radical, and R represents a hydrogen atom, a methyl group, an acetyl group or an ethoxycarbonyl group.

4-Hydroxy-2,5-dimethyl-3(2H)-furanone is a potent flavor ingredient, currently sold under the tradename of Furaneol® (origin; Firmenich SA, Geneva, Switzerland). This product is a solid at room temperature, and its stability can be affected by moisture and oxygen. The delivery systems according to the instant invention make it possible to protect this product from degradation for long periods of time and to provide it in a form where it can be rapidly and efficiently released upon use. The extruded Furaneol® flavor ingredient is not only more stable during storage but also of an easier application in consumer products than its prior known forms commercially available heretofore, i.e. in crystalline or solid form.

Furthermore, we have been able to establish that this extruded solid product, prepared according to the instant invention, is clearly preferred by the flavorists for its improved organoleptic properties, as will become apparent from the examples presented further on. We were in fact surprised to observe that the caramel, brown and sweetener effect typical of this compound was distinctly enhanced when Furaneol® was encapsulated according to the invention in a maltodextrin-type matrix. This enhancement effect can easily double the organoleptic effect imparted by solid or crystalline pure Furaneol® as prior commercialized. Furthermore, it was also accompanied by a distinctly perceived enhanced mouthfeel and masking effect. In other words, the presently disclosed extrusion formed Furaneol® products provide a fuller and stronger impact in the mouth and are even more capable of covering the taste, and particularly any off-notes, of the base of the edible products (foods, beverages, pharmaceuticals, toothpastes and washes, etc . . . ) into which they are incorporated. They therefore constitute preferred flavoring ingredients or solid delivery systems according to the invention.

The delivery systems of the invention are also particularly adapted for releasing any hydrophilic derivative of Furaneol® of current use in the flavor and/or fragrance industry, namely a compound of formula:

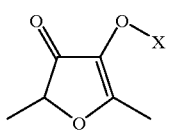

(I)

wherein X designates a linear or branched, saturated or unsaturated $C_1$–$C_5$ hydrocarbon radical or a group of formula:

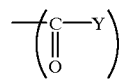

wherein Y designates a linear or branched, saturated or unsaturated $C_1$–$C_6$ hydrocarbon radical. The esters of formula (I) are described in U.S. Pat. No. 4,889,735.

Other derivatives of Furaneol® are particularly improved by the encapsulation system of the present invention, such as a compound of formula:

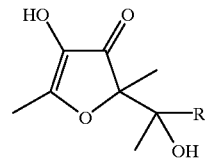

(II)

wherein R represents a hydrogen atom, a methyl group, an acetyl group or an ethoxycarbonyl group, whose preparation is described in U.S. Pat. No. 4,070,381.

Other non-limiting examples of hydrophilic materials advantageously used in the delivery systems of the invention include 3-hydroxy-4,5-dimethyl-2(5H)-furanone (also known as sotolone), 3-hydroxy-2-methyl-4(4H)-pyranone (also known as maltol), 4-hydroxy-5-methyl-3(2H)-furanone, 3-hydroxy-2-ethyl4(4H)-pyranone (also known as ethyl maltol) and 2-hydroxy-2-penten-4-olide.

All of the above-mentioned products are preferred according to the invention. They are chemically reactive aroma materials and their lability renders them hard to be encapsulated in a matrix. In the present invention, these active aroma ingredients are advantageously retained throughout the matrix in a homogeneous manner and thus they become far more resistant to moisture degradation and to oxidation. Moreover, the content in hydrophilic aroma of the solid delivery system varies in a wide range of values and can go up to 60% by weight of the dried extruded product, which is really an unexpected result with such labile products.

Vanillin, ethyl vanillin and piperonal, all current flavor ingredients, have also been successfully improved by incorporation according to the invention in an extrudable matrix.

Powdered hydrophilic plant extracts such as those from Gingko Biloba, Garcina Cambogia, St. John's Wort and Kava Kava contain active ingredients reported to have beneficial effects on the user. When encapsulated in an extruded matrix according to the present invention, they form dry, easy to handle products, wherein the active ingredients are protected from decomposition. It is to be noted that such powdered plants extracts, prior to being treated according to the invention, are difficult to handle and incorporate into dry applications, i.e. foods and other solid products such as chewing-gums, toothpastes and pharmaceuticals, without significant dusting. Encapsulation within a carbohydrate glass, as hereby disclosed, results in a dry, stable granulated product which eliminates this problem.

Another natural, purified extract, which is an example of an hydrophilic aroma ingredient capable of being processed according to the invention is inulin, or fructooligosaccharides, a product composed of a glucose molecule linked to 2, 3 or 4 fructose molecules (origin: Maypro Industries, Inc., Harrison, N.Y.).

Mixtures of one or more of the hydrophilic ingredients cited can also be used with advantage. In fact, we have observed organoleptic synergies and startling enhancement of the flavoring properties of some of the above cited ingredients when they are extruded together in the matrices according to the invention. In this context, one should cite in particular the mixtures of Furaneol® with maltol (3-hydroxy-2-methyl4(4H)-pyranone) and ethyl maltol (3-hydroxy-2-ethyl-4(4H)-pyranone). As it will become apparent from the examples presented further on, small amounts of Furaneol® can advantageously partially replace the latter, and namely ethyl maltol, to provide, once the mixture of Furaneol® and ethyl maltol is processed in an extruded solid product according to the invention, sweetening and flavoring effects characteristic of ethyl maltol but far stronger and more effective in the flavor enhancement and in the masking of any off-notes of the edible product in which they are used as flavorants than those which are observed when ethyl maltol is used on its own to form extruded flavoring systems according to the instant invention. Such extruded mixtures of Furaneol® with ethyl maltol or maltol shall preferably contain from about 0.2 to 25% by weight of ethyl maltol and from 1 to 25% by weight of maltol.

As the matrix in the delivery systems of the invention, there can be used any sugar or sugar derivative which can be readily processed through extrusion techniques to form a dry extruded solid. Particular examples of suitable materials include those selected from the group consisting of sucrose, glucose, lactose, levulose, fructose, maltose, ribose, dextrose, isomalt, sorbitol, mannitol, xylitol, lactitol, maltitol, pentatol, arabinose, pentose, xylose, galactose, hydrogenated starch hydrolysates, maltodextrin, Stabilite® (origin: SPI Polyols, USA), agar, carrageenan, other gums, polydextrose and derivatives and mixtures thereof.

According to a preferred embodiment of the invention, there will be used maltodextrin or mixtures of maltodextrin and at least one material selected from the group consisting of sucrose, glucose, lactose, levulose, maltose, fructose, isomalt, sorbitol, mannitol, xylitol, lactitol, maltitol and hydrogenated starch hydrolysates, preferably a maltodextrin having a dextrose equivalent not above twenty ($\leq 20$ DE) and more preferably a DE of 18.

The above-mentioned matrix compositions are hereby given by way of example and they are not to be interpreted as limiting the invention. Although polysaccharides are mentioned above as specific examples, it is clear that any material which is extrudable and currently used as a matrix material in the production of extruded solids appropriate for flavor applications is adequate for the aim of the invention and is therefore hereby included in the latter.

Following preferred embodiments of this invention, there will be used matrices which include maltodextrin. The latter can be the main material of the matrix, or yet be used in admixture with any one of the sugars mentioned above and, more preferably sucrose. Therefore in preferred embodiments the delivery system of the invention consists of a maltodextrin based matrix and 4-hydroxy-2,5-dimethyl-3 (2H)-furanone (Furaneol®), the proportion of the latter being at least about 10% by weight. Mixtures of Furaneol® with ethyl maltol, maltol or both, in the same matrix materials are also prime flavoring or aroma systems according to the invention, particularly effective for flavor enhancement and off-notes masking.

An emulsifier agent is preferably added to the mixture constituted by the matrix components and the hydrophilic aroma material. Suitable emulsifiers for use within the present invention include lecithin, sucrose esters of fatty acids and citric acid esters of fatty acids. Other suitable emulsifiers are cited in reference texts such as G. L. Hasenhuettl and R. W. Hartel, Food emulsifiers and their applications, 1997.

The extruded aroma ingredients and compositions of the invention can be produced by a method which is modified from the current extrusion methods known in the art in that a substantial amount of hydrophilic aroma composition is blended with the matrix materials before extrusion.

Thus, the invention also concerns a process for preparing a stable melt-based, extruded aroma delivery system, which comprises the steps of:

a) combining and blending a substantially hydrophilic aroma with an extrudable matrix material, an emulsifier and optionally a plasticizer under temperature and stirring conditions useful to produce a uniform melt thereof;

b) extruding the molten mass through a die;

c) chopping, cutting, grinding or pulverizing the material obtained as it exits the die or after having cooled the molten mass, and d) optionally drying.

According to a preferred embodiment of the process of the invention, step a) is carried out by heating a stirred mixture of the matrix material, the hydrophilic aroma, the emulsifier and a certain amount of water to about the melting point of this aqueous mixture, thus obtaining the homogeneous melt.

Typical conditions for this process are similar to those of processes for encapsulating hydrophobic flavors, as described for example in U.S. Pat. Nos. 4,610,890 and 4,707,367, the contents of which are hereby included by reference. The products obtained by this type of methods are based on the formation of a melt and extrusion of the latter at an appropriate temperature. Typically, the hydrophilic material or composition is combined and blended with an aqueous mixture of a sugar, a starch hydrolysate and an emulsifier, and this aqueous mixture is then heated to the boiling point of water or a temperature slightly above, but preferably not above 130° C., to form a homogeneous melt, which is then extruded into a die. The molten mass which exits the die can then either be chopped as it is still in a plastic state (melt granulation or wet granulation techniques), or be cooled in a liquid solvent to form the extruded solid, the shape and size of which can be adjusted as a function of the extrusion parameters before being grinded. The particulate solid obtained by extrusion can be dried, if needed, by means of an anticaking agent such as silicon oxide, for example. The temperature and pressure conditions under which this process is carried out are current and fully described in the US documents cited above, the teachings of which are hereby included by reference and form an integrant part of the present specification. Such parameters can therefore be adjusted by the skilled person without particular effort and as a function of the nature of the ingredients present in the melt and of the quality of the product which is desired to obtain, i.e. its granulometry and shape.

The type and design of the equipment used requires no detailed description here, the expert in this field being well-acquainted with current apparatuses, their technical specificities and the choice of appropriate equipment for a desired specific shape and size of extruded solid. It is well-known, moreover, that such extruded solids may be produced in many forms, i.e. powders of varied granulometry, rods, flakes, filaments, etc. Techniques such as grinding (or criogrinding), pulverizing or sieving are also known to further provide for reduction of the size of the extruded solid, namely in the case of extruded particulate solids, to reduce it to the state of fine micromized powders, if so desired.

According to another extrusion method adequate for producing the delivery systems of the invention, there is no need in step a) to first blend the hydrophilic aroma material and the matrix material with a large amount of water to obtain an homogeneous melt. It is possible in fact to heat a substantially solid mixture of these ingredients, containing only a small amount of plasticizer, to its melting temperature, and to press-feed the extruder with this substantially solid mass, under efficient mixing, to ensure formation of an homogeneous melt and obtain a stable extruded product. The so-called "dry-blend" and "flash-flow" extrusion techniques obey this principle, and they typically require the use of higher pressures to feed the melt of the originally essentially solid material through the extruder than the methods cited above which resort to the extrusion of substantially liquid or fluid molten mixtures of ingredients.

Thus, in the processes described in the above-mentioned patents and in the prior art in general, the homogeneous mixture of flavour material and carbohydrate matrix prepared in the first step of the process is heated within the screw-extruder in such a way that the temperature of the mixture is above the glass transition temperature of the matrix in order to form a molten mass. Then, the molten mass is extruded through a die.

As mentioned above the next step c) depends on the technique used. The molten mass can be cooled as it exits the die to a temperature below the glass transition temperature of the matrix. It thus provides a solid extruded material in the form of filaments. Extruded granules can then be manufactured by breaking the extruded material cooled below its glass transition temperature. This crushing step unavoidably loses a certain amount of matter because of the hardness of the material and it can also happen that the encapsulated volatile compound is damaged and partially lost during this step.

In other cases, wet-granulation is used to chop the extruded product as it is still in a plastic state above its glass transition temperature. For instance EP 202409 describes a method for the production of stable, spherical particles of viable micro-organisms which comprises the steps of mixing a culture concentrate with a bulking agent to form a homogeneous wet granulate, extruding the wet granulate through a die to produce filaments having a diameter of approximately the size of the desired spheres and then using a spheroniser device which comprises a plate that rotates at a tangential speed sufficient to cause the filaments to be shaped into discrete spherical particles, and finally drying the particles. Before the drying step, the glass transition temperature of the extruded mass is relatively low because of the large proportion of water used as plasticizer. The additional drying step is thus necessary to evaporate some water from the system, thus increasing the Tg to a sufficient value to provide a product capable of being stored at room temperature.

However, the prior art wet-granulation process as mentioned hereinabove requires an additional drying step to increase Tg to an acceptable value. On the other hand, the crushing step of an extruded material cooled below its glass transition provides matrix encapsulates which are rarely uniform in size. In fact, this last method leads to size distribution of particles in matrix type powders and granules which follows generally a large gaussian distribution. Yet, depending on the application intended for the extruded product, the ability to control the size and homogeneity of the extruded material may be of paramount importance. It is then very important to be able to obtain a narrow size distribution with a minimum of capsules being larger or smaller than the average size desired for the intended purpose. Moreover, it may also be very important to optimise the yield of the manufactured granules, i.e. to minimise losses during the granulation process.

Thus, according to one embodiment of the present invention particularly adapted to matrices which contain a small amount of water, there are provided solid delivery systems for the release of aroma ingredients which are prepared via a process according to which the uniform melt produced in step a) is obtained by heating the mixture of matrix material and hydrophylic aroma to a temperature comprised between 90 and 130° C., the mixture being then subsequently extruded through a die and the molten mass being chopped as it exits the die and before it is cooled to solidify.

According to this particular embodiment, a low water content is added to the mixture to be melt to guarantee that the glass transition temperature Tg of the resulting melt corresponds to and is substantially the same as that of the desired Tg value of the final product. In other words, contrary to other methods such as wet-granulation, the glass transition temperature of the mixture before extrusion has already the value required for the final product, which temperature is above room temperature and preferably above 40° C. so that the product can be stored at ambient temperature in the form of free-flowing granules. As a consequence, this embodiment of the invention can dispense with the additional drying step following the extrusion, intended to remove water in order to increase Tg to an acceptable value.

The mixture is thus extruded in an extruder assembly which maintains the temperature of the mixture at a predetermined temperature which is comprised between 90 and 130° C. This temperature is adapted to the system of the invention: first of all, it has to be above the glass transition temperature of the carbohydrate matrix in order to keep the mixture in the form of a molten mass. Pressure is also applied and adjusted to a value appropriate to maintain homogeneity of the melt. Typically, pressure values of up to 100 bar ($10^7$ Pa) can be used, preferred values lying in the range of 1 to 20 bar ($10^5$ to $2 \times 10^6$ Pa).

In this particular embodiment, as the mixture comes to the die part of the extruder, the temperature is still above the glass transition temperature of the carrier. The extruder is equipped with a cutterknife and the mixture is thus cut at the temperature of the melt. Once cooled to ambient temperature by the surrounding air, the already cut glassy material does not need to be shaped and dried in a spheroniser or other device, unlike what is the case with other processes where the molten matrix is cooled prior to the cutting.

The preferred process according to the invention wherein step c) is carried out at the temperature of the melt, thus provides capsules with a uniform size. This embodiment of the process according to the invention is very advantageous because the release of volatile compounds such as flavour compounds is defined by the physico-chemical properties of the matrix material and occurs generally through solution in a solvent or plasticiser, or through thermal or mechanical activation. The specific area of the matrix type delivery system is a parameter which influences the delivery process, a large specific area providing a high molecular flux in the case of a solvent activation. The release through dissolution is thus particularly dependent on the surface area of the particle. The kinetics of flavour delivery is monitored by the size of the solid particles manufactured by the granulation process. As a consequence, in order to provide a uniform kinetically well defined release of the volatiles entrapped, the capsules have further to present a narrow size distribution. We have discovered that this particular embodiment of the process according to the invention could advantageously allow the manufacture of extruded flavour systems in a granular form and with a narrow size distribution, and this in only one step after the extrusion process, thus dispensing with the cooling, drying and other further processing steps which are current in other methods.

The glass transition temperature of the volatile compound/carbohydrate mixture depends on the amount of water added to the initial mixture. In fact, it is well known in the art that the Tg decreases when the proportion of water increases. In the latter embodiment of the invention, the proportion of water added to the mixture will be low, i.e. such that the glass transition temperature of the resulting mixture is substantially equal to the glass transition temperature desired for the final flavour or fragrance delivery system, i.e. the extruded product. Now, as mentioned above, a requirement for the resulting encapsulated compound or composition is to present a glass transition temperature Tg significantly above the temperature at which it will be stored and subsequently used. The critical temperature must thus be at least above room temperature and preferably above 40° C. The proportions in which water is employed in the present invention therefore vary in a wide range of values which the skilled person is capable of adapting and choosing as a function of the carbohydrate glass used in the matrix and the required Tg of the final product.

For instance, for a carbohydrate glass having a DE (dextrose equivalent) of 18, proportions from 5 to 10% of water in the mixture can be used.

The softening or glass transition temperature is preferably kept above 40° C. to guarantee the free flowing nature of the produced powder samples at ambient temperature. A low water content to guarantee that the carrier's glass transition temperature is above room temperature and preferably above 40° C. is thus added to the mixture.

As cited before the extruding step of this process requires an extruding apparatus. A commercially acceptable extruding apparatus is that under the trade name designation Clextral BC 21 twin-screw extruder equipped with a cutterknife allowing to chop the melt at the die exit, when it is still plastic. However, extruding apparatuses are not limited to the twin screw variety and may also include, for example, single screw, ram, or other similar extrusion methods. The extrusion apparatus is equipped with a temperature regulation mechanism allowing to increase progressively the temperature of the mixture up to a value comprised typically between 90 and 130° C. at which point it can be extruded through the die holes.

During the extrusion process, the mixture is forced through a die having an orifice with a predetermined diameter which ranges from about 0.250 to 10 mm and preferably from 0.7 to 2.0 mm. However, much higher diameters for the die are also possible. The die orifice is at the same temperature as that the rest of the apparatus, and is equipped with a cutterknife or any other cutting device allowing to chop the melt as it exits from the die when it is still plastic. The product which is cut is thus still at a temperature which is above the glass transition temperature of the matrix.

The length of the pieces is regulated by controlling the stroke rate of the specific cutting apparatus.

The severed pieces are subsequently cooled to ambient temperature by the surrounding air. No drying or further treatment is needed. The resulting granules present a size uniformity and this size uniformity of the resulting capsules allows an improved control of flavour release.

According to this particular embodiment of the invention, where the granulation is carried out as the melt exits the die, there are thus obtained solid flavor delivery systems of substantially uniform granulometry.

As previously cited, these extruded solids of the invention are particularly appropriate for the delivery of hydrophilic flavoring or perfuming ingredients contained therein, and more preferably those hydrophilic aroma materials which are solid at room temperature or which can be rendered solid prior to the extrusion via spray-drying techniques for example. Said extruded solids are typically granulated products which are perfectly stable against moisture and oxygen and prevent degradation of the hydrophilic aroma ingredient or composition encapsulated therein. This is a result of the fact that the latter is homogeneously and uniformly distributed in the amorphous extruded matrix and perfectly incorporated within. These granulated products are far easier to handle, as they produce no significant amounts of dust when processed into the foods, powder beverages, chewing-gums, pharmaceuticals and other edibles and consumer products into which they are incorporated.

Amongst the solids thus obtained according to the invention, the extruded solids of Furaneol®, 3-hydroxy4,5-dimethyl-2(5H)-furanone, 4-hydroxy-5-methyl-3(2H)-furanone, 3-hydroxy-2-methyl-4(4H)-pyranone, 2-ethyl-3-hydroxy-4(4H)-pyranone, 2-hydroxy-2-penten4-olide and a compound of formula:

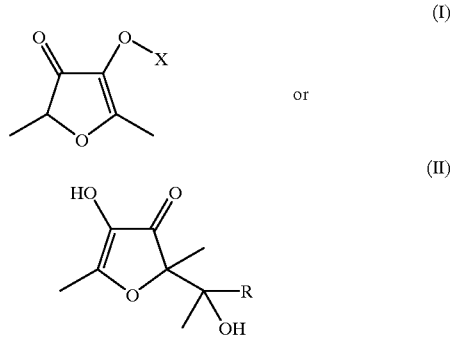

wherein X designates a linear or branched, saturated or unsaturated $C_1$–$C_5$ hydrocarbon radical or a group of formula:

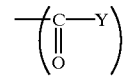

wherein Y designates a linear or branched, saturated or unsaturated $C_1$–$C_6$ hydrocarbon radical, and R represents a hydrogen atom, a methyl group, an acetyl group or an ethoxycarbonyl group, cited earlier are prime products of the invention, forming flavor systems of advantageous use over their prior known commercial forms.

The content in hydrophilic aroma component of the solid delivery systems of the invention varies in a wide range of values, typically of up to 60% by weight of the dried extruded product, and is preferably comprised between 5 and 35% by weight of the extruded solid delivery system.

This high content in hydrophilic active ingredient renders the delivery systems of the invention cost-effective, which is another advantage of their use.

Furthermore, as is apparent from the examples presented further on, hydrophilic flavoring ingredients according to the invention can advantageously replace, partially or totally, the sugar component typically present in maltodextrin-based matrices, thus providing non-cariogenic flavoring compositions for use in low-sugar or sugar-free foods.

It is also to be noted that the invention further provides solid systems for the delivery of hydrophilic ingredients such as plant extracts and other active substances which are not only useful to impart or modify the taste of foodstuffs and other products susceptible of entering the mouth of individuals and animals, but also contain, or constitute, active principles capable of providing other beneficial effects for the consumer. Examples of delivery systems of the invention containing such nutraceutical-type plant extracts and substances can be found hereafter.

It goes without saying that, although the delivery systems of the invention are particularly advantageous for delivering hydrophilic aroma ingredients, they can also be used to further encapsulate hydrophobic compositions, and namely flavor oils and fragrance oils, as long as the latter are compatible, from an organoleptic and/or hedonic point of view, with the hydrophilic aroma ingredient or ingredients present in a given delivery system.

The instant extruded solids can be advantageously used to impart or modify the organoleptic properties of a great variety of edible products, i.e. foods, beverages, pharmaceuticals and the like. Their incorporation in chewing-gums and toothpastes is straightforward and provides improved effects. In a general manner, they enhance the typical organoleptic effect of the corresponding unextruded hydrophilic flavor material and they are more effective than the latter in the coverage and masking of any off-notes present in the food or beverage, such as for example the bitter notes of coffee and tea-based beverages, the sour notes of soya-based edible products or of certain cereal or flour-based foods, or yet metallic notes detectable for example in mint flavored sweets and candies.

The concentrations in which they can be incorporated in such consumer products vary in a wide range of values, which are dependent on the nature of the product to be flavored and that of the particular delivery system of the invention used.

Typical concentrations, to be taken strictly by way of example, are comprised in a range of values as wide as from a few p.p.m. (parts per million) up to 5 or even 10% of the weight of the flavoring composition or finished consumer product into which they are included.

Adjuvant s such as for example food grade colorants can also be added in a generally known manner, to the extrudable mixtures of the invention so as to provide colored flavor systems and granulates.

The invention will now be described in further detail by way of the following examples.

EMBODIMENTS OF THE INVENTION

EXAMPLE 1

| Ingredient | grams |
|---|---|
| Maltodextrin 18 DE | 1360 |
| Sucrose | 1050 |
| Water | 600 |
| Furaneol ®[1] | 310 |
| Lecithin | 30 |

[1] 4-hydroxy-2,5-dimethyl-3(2H-furanone; origin: Firmenich SA, Geneva, Switzerland The maltodextrin and sucrose were dissolved in water and heated to 126° C. to reduce the water content to approximately 7%. Furaneol® and lecithin were added and mixed to form a uniform melt. The mixture was extruded under 2 bar pressure through a die plate with 2 mm holes. Once dried, 1% silicon dioxide was added as a free flow agent. The final product contained 9.1% Furaneol® by weight, 3.9% moisture and had a glass transition temperature of 35.7° C. After 7 months storage at 37° C., the Furaneol® content was 9.0% by weight.

EXAMPLE 2

| Ingredient | grams |
|---|---|
| Maltodextrin 18 DE | 1360 |
| Sucrose | 610 |
| Water | 600 |
| Furaneol ®[1] | 750 |
| Lecithin | 30 |

[1] 4-hydroxy-2,5-dimethyl-3(2H)-furanone; origin: Firmenich SA, Geneva, Switzerland Preparation was the same as in Example 1. The finished product contained 25.0% Furaneol® by weight.

EXAMPLE 3

Composition and procedure were the same as Example 1 except that Furaneol® was replaced with maltol (3-hydroxy-2-methyl-4(4H)-pyranone). Initial assay showed 11.1% maltol, 4.6% moisture and a glass transition temperature of 38.2° C. After 10 months storage at 37° C., maltol content was 11.0% by weight.

EXAMPLE 4

| Ingredient | grams |
|---|---|
| Maltodextrin 18 DE | 1360 |
| Sucrose | 650 |
| Water | 600 |
| Maltol[1] | 1080 |
| Lecithin | 32 |

[1] "Corps praline"; origin: Firmenich SA, Geneva, Switzerland

Procedure was the same as in Example 1.

EXAMPLE 5

| Ingredient | grams |
|---|---|
| Maltodextrin 18 DE | 1250 |
| Sucrose | 750 |
| Water | 600 |
| Gingko Biloba extract | 2000 |
| Lecithin | 35 |

Gingko Biloba extract was dissolved in water with the sucrose and maltodextrin. Remaining procedure was the same as Example 1. The final product contained 120 mg/g flavonoglycosides and 40 mg/g terpenoids, 3.8% moisture and a glass transition temperature of 37.1° C.

EXAMPLE 6

| Ingredient | grams |
|---|---|
| Maltodextrin 18 DE | 1000 |
| Sucrose | 1300 |
| Water | 600 |
| Fructooligosaccharides | 420 |
| Lecithin | 15 |

The fructooligosaccharides were dissolved in water with the sucrose and maltodextrin. Remaining procedure was the same as Example 1. The final product had a 5.34% moisture content and a glass transition temperature of 33.9° C.

EXAMPLE 7

| Ingredient | grams |
| --- | --- |
| Maltodextrin 18 DE | 37 |
| Garcinia Cambodia extract | 55 |
| Lecithin | 1 |
| Water | 7 |

The maltodextrin was dry-blended with Garcinia Cambodia extract and lecithin. The resulting free flowing powder was granulated at 113° C. and under 10 bar pressure through a 2 mm die using a twin-screw extruder. The final product contained 55% Garcinia Cambodia and 7% water by weight corresponding to a glass transition temperature of 48° C.

EXAMPLE 8

| Ingredient | grams |
| --- | --- |
| Maltodextrin 18 DE | 47 |
| Liquorice extract | 47 |
| Lecithin | 1 |
| Water | 5 |

The maltodextrin was dry-blended with Liquorice extract and lecithin. The resulting free flowing powder was granulated at 120° C. and under 20 bar pressure through a 2 mm die using a twin-screw extruder. The final product contained 47% Liquorice extract and 5% water by weight corresponding to a glass transition temperature of 49° C.

EXAMPLE 9

| Ingredient | grams |
| --- | --- |
| Maltodextrin 18 DE | 43 |
| Instant Coffee | 43 |
| Lecithin | 1 |
| Water | 3 |

The maltodextrin was dry-blended with Instant Coffee and lecithin. The resulting free flowing powder was granulated at 110° C. and under 10 bar pressure through a 2 mm die using a twin-screw extruder. The final product contained 43% Instant Coffee and 3% water, by weight, corresponding to a glass transition temperature of 35° C.

EXAMPLE 10

| Ingredient | grams |
| --- | --- |
| Maltodextrin 18 DE | 71 |
| Capsul ®[1)] | 08 |
| Honey | 16 |
| Lecithin | 1 |
| Water | 4 |

[1)]modified corn starch; origin: National Starch, USA

The maltodextrin was dissolved in water, Honey and lecithin were added to the solution, which was dehydrated by spray drying. The resulting free flowing powder was granulated at 110° C. and under 22 bar pressure through a 2 mm die using a twin-screw extruder. The final product contained 16% Honey and 4% water, by weight, corresponding to a glass transition temperature of 57° C.

EXAMPLE 11

| Ingredient | grams |
| --- | --- |
| Maltodextrin 18 DE | 80 |
| Crystalline citric acid | 15 |
| Lecithin | 1 |
| Water | 4 |

The maltodextrin was dissolved in water, citric acid and lecithin were added to the solution, which was dehydrated by spray drying. The resulting free flowing powder was granulated at 125° C. and under 20 bar pressure through a 2 mm die using a twin-screw extruder. The final product contained 15% amorphous citric acid and 4% water, by weight, corresponding to a glass transition temperature of 48° C.

EXAMPLE 12

| Ingredient | grams |
| --- | --- |
| Maltodextrin 18 DE | 83 |
| Crystalline maleic acid | 12 |
| Lecithin | 1 |
| Water | 4 |

The maltodextrin was dissolved in water, maleic acid and lecithin were added to the solution, which was dehydrated by spray drying. The resulting free flowing powder was granulated at 110° C. and under 22 bar pressure through a 2 mm die using a twin-screw extruder. The final product contained 12% amorphous maleic acid and 4% water, by weight, corresponding to a glass transition temperature of 44° C.

EXAMPLE 13

| Ingredient | grams |
| --- | --- |
| Maltodextrin 18 DE | 75 |
| Dehydrated Orange juice conc.[1)] | 20 |
| Lecithin | 1 |
| Water | 4 |

[1)]ex 60 Brix natural fruit juice concentrate

The maltodextrin was dissolved in water, orange juice concentrate (33% water) and lecithin were added to the solution, which was dehydrated by spray drying. The resulting free flowing powder was granulated at 102° C. and under 9 bar pressure through a 2 mm die using a twin-screw extruder. The final product contained 21% orange juice solids and 4% water, by weight, corresponding to a glass transition temperature of 47° C.

EXAMPLE 14

| Ingredient | grams |
| --- | --- |
| Maltodextrin 18 DE | 82 |
| Furaneol ® | 10 |
| Lecithin | 1 |
| Water | 7 |

The maltodextrin was dissolved in water, Furaneol® and lecithin were added to the solution which was dehydrated by spray drying. The resulting free flowing powder was granulated by dropping the melt at 98° and under $5 \times 10^5$ Pa pressure as it exits the die holes through a 2 mm die using a twin screw extruder. The final product contained 11% Furaneol® and 7% water, by weight, corresponding to a glass transition temperature of 44°.

EXAMPLE 15

| Ingredient | grams |
| --- | --- |
| Isomalt | 600 |
| Stabilite ® | 2640 |
| Furaneol ® | 310 |
| Acacia Gum | 90 |
| Lecithin | 1 |
| Water | 400 |

The acacia gum was dissolved in a 1:3 aqueous solution. Stabilite®, isomalt and water were added. The mixture was heated to 148°. Furaneol® and lecithin were added and mixed to form a uniform melt. The mixture was extruded through a die plate with 850 micron holes. Once dried, 1% silica was added as a free flow agent. The final product contained 9% Furaneol® by weight and a 4% moisture content. The reducing sugars content was less than 2%.

EXAMPLE 16

| Ingredient | grams |
| --- | --- |
| Maltodextrin 18DE | 2940 |
| Sucralose ®[1] | 60 |
| Water | 800 |

[1] 1,6-dichloro-1,6-dideoxy-beta-D-fructofuranosyl-4-chloro-alpha-D-galacto-pyranoside; origin: McNeil Speciality Products Co., New Brunswick, USA The maltodextrin was dissolved in water and heated to 110° to reduce the moisture to approximately 10%. Sucralose® was added and mixed to uniformity. The mixture was extruded under $4 \times 10^5$ Pa pressure through a die plate with 1 mm holes then dried to reduce moisture further. The product appeared as semi translucent particles similar in appearance to granulated sugar. Initial assay showed 2% Sucralose® and 6.4% moisture, glass transition temperature of 65°.

EXAMPLE 17

| Ingredient | grams |
| --- | --- |
| Maltodextrin 18DE | 1383 |
| Sucrose | 492 |
| Sucralose ®[1] | 843 |
| Lecithin | 24 |
| Lemon oil | 258 |
| Water | 600 |

[1] see example 16

The maltodextrin, sucrose and Sucralose® were dissolved in water and heated to 118° to reduce moisture to approximately 6%. The mixture was extruded under $3 \times 10^5$ Pa pressure through a die plate with 1 mm holes. Once dried, 1% silicone dioxide was added as free flow agent. The final product was assayed and found to contain 28% Sucralose®, 8.5% lemon oil and 4.8% moisture, by weight and to have a glass transition temperature of 44°.

EXAMPLE 18

Comparative tests were carried out with the delivery system described in Example 1, and with commercial available Furaneol® (Furaneol® NI; origin; Firmenich SA, Geneva, Switzerland).

To this end, a group of 30 consumer panelists evaluated on a blind test two solutions in flat water, containing identical concentrations of Furaneol®, solution A comprising commercial Furaneol®, and solution B the delivery system according to Example 1. The panel indicated an almost unanimous preference for solution B, which was judged to have an increased overall impact in the mouth and a taste wherein the cotton candy, caramelic, syrupy and fruity type connotations typical of Furaneol® were clearly reinforced, relative to those of solution A. Furthermore, the taste of solution B was more balanced and full bodied, with an appreciated stronger candy and syrupy character.

EXAMPLE 19

An extruded solid sample of Furaneol®, prepared according to Example 1 or 2, was incorporated in a roast chicken type flavor, i.e. Firanova® RC 587052 (origin: Firmenich SA, Geneva, Switzerland) at such a concentration that Furaneol® was present at 30 ppm, relative to the total weight of the chicken type flavor composition, to prepare a novel chicken flavor A.

In parallel, commercially available Furaneol® (Furaneol® NI, origin: Firmenich SA, Geneva, Switzerland) was added to the same chicken flavor, in identical concentration, to prepare a flavor B for comparison.

The two compositions A and B were then evaluated on a blind test by a panel of 30 consumers. The results of the test showed that flavor B was preferred by a statistically significant majority of the panelists. In the opinion of the latter, this preferred flavor was more full-bodied, more balanced and rounded than flavor A, the roast chicken character also appearing as having been enhanced, the overall flavor being also perceived as more powerful than flavor A.

EXAMPLE 20

| Ingredient | grams |
|---|---|
| Maltodextrin 18DE | 340 |
| Maltodextrin 5DE | 1020 |
| Sucrose | 610 |
| Water | 1200 |
| Ethyl maltol[1] | 455 |
| Furaneol ®[2] | 300 |
| Lecithin | 10 |
| Sum (w/o water) | 2735 |

[1] Corps praline; origin: Firmenich SA, Geneva, Switzerland
[2] 4-hydroxy-2,5-dimethyl-3(2H)-furanone; origin: Firmenich SA, Geneva, Switzerland Preparation was the same as in Example 1. Except that the die plate had 0.50 nim holes. The initial assays showed 9.9% Furaneol®, 14.1% ethyl maltol, and 3.2% water content. The glass transition temperature was 43.2° C.

When compared on a blind test with an extruded product obtained in a similar manner but containing only ethyl maltol, in a concentration of about 25% by weight, the above product was unanimously preferred by a panel of flavorists. The latter indicated that its perceived sweetness and flavoring effect had increased by a factor of at least 2.

Similar flavor enhancement could be observed in extruded products having a similar composition but wherein ethyl maltol was replaced by maltol.

What is claimed is:

1. A solid delivery system for the release of aroma ingredients, comprising an extrusion formed matrix comprising a sugar or sugar derivative that can be extruded to a dry solid, the matrix containing an effective amount of substantially hydrophilic aroma material selected from the group consisting of 3-hydroxy-4,5-dimethyl-2(5H)-furanone, 4-hydroxy-2,5-dimethyl-3(2H)-furanone, 4-hydroxy-5-methyl-3(2H)-furanone, 3-hydroxy-2-methyl-4(4H)-pyranone, 2-ethyl-3-hydroxy-4(4H)-pyranone, 2-hydroxy-2-penten-4-olid, and a compound of formula:

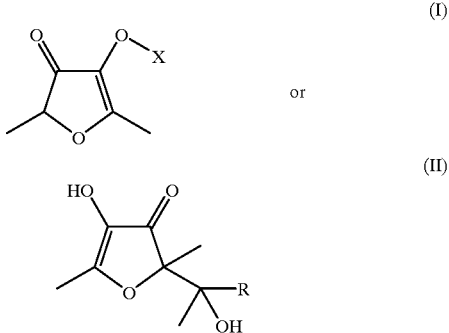

wherein X designates a linear or branched, saturated or unsaturated C1–C5 hydrocarbon radical or a group of formula:

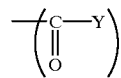

wherein Y designates a linear or branched, saturated or unsaturated $C_1$–$C_6$ hydrocarbon radical, and R represents a hydrogen atom, a methyl group, an acetyl group or an ethoxycarbonyl group, and mixtures or derivatives thereof.

2. The delivery system of claim 1, wherein the matrix is selected from the group consisting of sucrose, glucose, lactose, levulose, fructose, maltose, ribose, dextrose, isomalt, sorbitol, mannitol, xylitol, lactitol, maltitol, pentatol, arabinose, pentose, xylose, galactose, hydrogenated starch hydrolysates, maltodextrin, hydrogenated starch agar, carrageenan, gums, polydextrose and derivatives and mixtures thereof.

3. The delivery system of claim 2, wherein the matrix is formed of maltodextrin or of a mixture of maltodextrin and at least one material selected from the group consisting of sucrose, glucose, lactose, levulose, maltose, fructose, isomalt, sorbitol, mannitol, xylitol, lactitol, maltitol and hydrogenated corn syrup.

4. The delivery system of claim 3, wherein the matrix includes maltodextrin.

5. The delivery system according to claim 1, wherein the hydrophilic aroma material is present in the extruded matrix in a concentration ranging from about 5% to about 40% by weight.

6. A delivery system according to claim 1, which further contains a hydrophobic flavor or fragrance oil.

7. A delivery system according to claim 6, wherein the flavor oil is selected from the group consisting of citrus and other fruit oils, mint oils, nut oils and mixtures thereof.

8. A solid delivery system for the release of aroma ingredients, comprising an extrusion formed matrix comprising a maltodextrin, the matrix containing an effective amount of 4-hydroxy-2,5-dimethyl-3(2H)-furanone, or a mixture of the latter with maltol or ethyl maltol.

9. A delivery system according to claim 8, containing at least about 10% by weight of 4-hydroxy-2,5-dimethyl-3(2H)-furanone.

10. A delivery system according to claim 8, containing from about 0.2 to about 25% by weight of ethyl maltol.

11. A delivery system according to claim 8, containing from about 1 to about 25% by weight of maltol.

12. A delivery system according to claim 9, which further contains maltol or ethyl maltol.

13. A delivery system according to claim 8, wherein said maltodextrin-based matrix includes a maltodextrin that has a DE of less than 20.

14. A delivery system according to claim 8, wherein said maltodextrin-based matrix includes a maltodextrin that has a DE of about 18.

15. A foodstuff, a beverage, an edible composition, a pharmaceutical composition, a nutraceutical composition, a chewing-gum or a toothpaste, containing a delivery system as defined in claim 1.

16. The delivery system of claim 4, wherein said maltodextrin-based matrix includes a maltodextrin that has a DE of less than 20.

17. A foodstuff, a beverage, an edible composition, a pharmaceutical composition, a nutraceutical composition, a chewing-gum or a toothpaste, containing a delivery system as defined in claim 8.

* * * * *

UNITED STATES PATENT AND TRADEMARK OFFICE
CERTIFICATE OF CORRECTION

PATENT NO. : 6,607,778 B2
DATED : August 19, 2003
INVENTOR(S) : Mutka et al.

It is certified that error appears in the above-identified patent and that said Letters Patent is hereby corrected as shown below:

<u>Title page,</u>
Item [75], Inventors, change the address of inventor "Daniel Benczedi" from "Geneva (CH)" to -- Carouge (CH) --.

Signed and Sealed this

Ninth Day of December, 2003

JAMES E. ROGAN
*Director of the United States Patent and Trademark Office*